(12) United States Patent
Crawford et al.

(10) Patent No.: US 11,974,795 B2
(45) Date of Patent: May 7, 2024

(54) SURGICAL ROD BENDING SYSTEM AND METHOD

(71) Applicant: DIGNITY HEALTH, San Francisco, CA (US)

(72) Inventors: Neil R. Crawford, Tempe, AZ (US); Nicholas Theodore, Paradise Valley, AZ (US); Philip M. Reyes, Mesa, AZ (US); Anna G. U. S. Newcomb, Tempe, AZ (US); Seungwon Baek, Phoenix, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 0 days.

(21) Appl. No.: 17/526,302

(22) Filed: Nov. 15, 2021

(65) Prior Publication Data
US 2022/0142677 A1    May 12, 2022

Related U.S. Application Data

(60) Continuation of application No. 16/292,527, filed on Mar. 5, 2019, now Pat. No. 11,172,971, which is a
(Continued)

(51) Int. Cl.
*A61B 17/88*    (2006.01)
*A61B 17/70*    (2006.01)
(Continued)

(52) U.S. Cl.
CPC .......... *A61B 17/8863* (2013.01); *B21D 7/022* (2013.01); *B21D 7/08* (2013.01); *B21D 43/006* (2013.01); *B21F 1/008* (2013.01); *B21F 23/005* (2013.01); *B21F 45/008* (2013.01); *A61B 17/7013* (2013.01)

(58) Field of Classification Search
CPC .......... B21D 7/02; B21D 7/022; B21D 7/024; B21D 7/025; B21D 7/04; B21D 7/06; B21D 7/08; B21D 7/12; B21D 7/14; B21D 9/10; B21D 11/10; B21D 11/22; B21D 43/003; B21D 43/006; B21F 1/004; B21F 1/006; B21F 1/008; B21F 23/005; B21F 45/008; A61B 17/8863
See application file for complete search history.

(56) References Cited

U.S. PATENT DOCUMENTS 3,661,002 A    5/1972    Peddinghaus
3,821,525 A    6/1974    Eaton
(Continued)

FOREIGN PATENT DOCUMENTS

WO    2011055505    5/2011

*Primary Examiner* — Peter Dungba Vo
*Assistant Examiner* — Joshua D Anderson
(74) *Attorney, Agent, or Firm* — QUARLES & BRADY LLP

(57) ABSTRACT

System and method for automatically bending a surgical rod are provided. The system includes a linear movement device configured to axially feed the surgical rod, a rotational movement device configured to rotate the surgical rod as it is axially fed, and a bending device including a roller to impose bending forces against the rod. The rod is free from contact with the bending device after it is axially fed past the roller.

13 Claims, 8 Drawing Sheets

Related U.S. Application Data continuation of application No. 15/467,751, filed on Mar. 23, 2017, now Pat. No. 10,219,852, which is a division of application No. 14/362,417, filed as application No. PCT/US2012/067924 on Dec. 5, 2012, now Pat. No. 9,636,162.

(60) Provisional application No. 61/566,891, filed on Dec. 5, 2011.

(51) Int. Cl.
| | | |
|---|---|---|
| *B21D 7/022* | (2006.01) | |
| *B21D 7/08* | (2006.01) | |
| *B21D 43/00* | (2006.01) | |
| *B21F 1/00* | (2006.01) | |
| *B21F 23/00* | (2006.01) | |
| *B21F 45/00* | (2006.01) | |

(56) References Cited

U.S. PATENT DOCUMENTS

| | | |
|---|---|---|
| 4,552,006 A | 11/1985 | Yogo |
| 4,785,650 A | 11/1988 | Lusty |
| 4,799,373 A | 1/1989 | Benton |
| 4,825,678 A | 5/1989 | Post |
| 5,144,829 A | 9/1992 | Fabro |
| 5,447,432 A | 9/1995 | Andreiko |
| 5,658,286 A | 8/1997 | Sava |
| 5,938,662 A | 8/1999 | Rinner |
| 6,035,691 A | 3/2000 | Lin |
| 6,434,995 B1 | 8/2002 | Kataoka |
| 7,957,831 B2 | 6/2011 | Isaacs |
| 9,636,162 B2 | 5/2017 | Crawford |
| 9,872,715 B2 | 1/2018 | Crawford |
| 10,194,968 B2 | 2/2019 | Crawford |
| 10,219,852 B2 | 3/2019 | Crawford |
| 2004/0072120 A1 | 4/2004 | Lauren |
| 2005/0262911 A1 | 12/2005 | Dankowicz |
| 2007/0227216 A1 | 10/2007 | Schalliol |
| 2009/0249851 A1 | 10/2009 | Isaacs |
| 2010/0116012 A1 | 5/2010 | Hermes |
| 2011/0192204 A1 | 8/2011 | Steinhilber |
| 2011/0259075 A1* | 10/2011 | Kirchmer ............ B21D 7/0225 72/389.1 |
| 2011/0295086 A1 | 12/2011 | Nakada |
| 2014/0076015 A1 | 3/2014 | Riemeier |

* cited by examiner

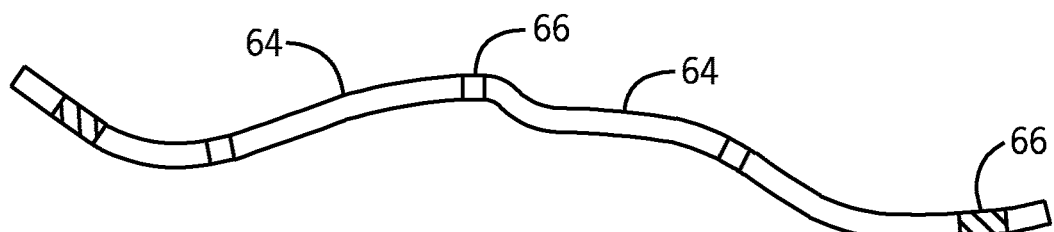
FIG. 9
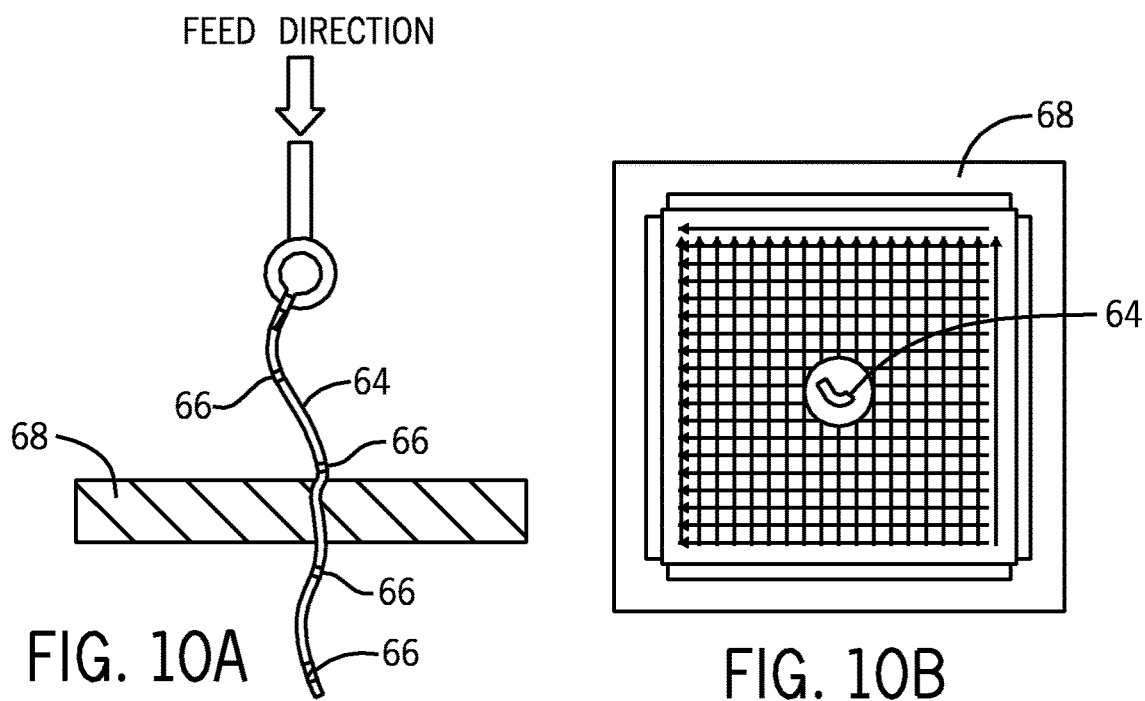
FIG. 10A
FIG. 10B
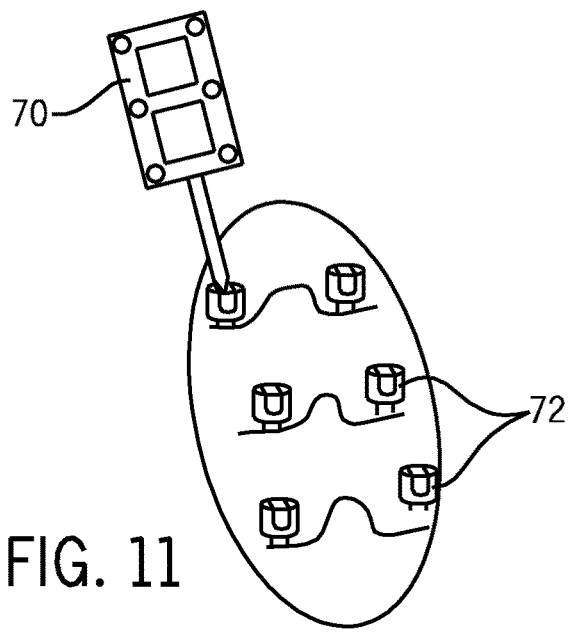
FIG. 11

SURGICAL ROD BENDING SYSTEM AND METHOD

CROSS REFERENCE TO RELATED APPLICATIONS

This application is a continuation of U.S. application Ser. No. 16/292,527, filed Mar. 5, 2019, which is a continuation of U.S. application Ser. No. 15/467,751 filed Mar. 23, 2017, now U.S. Pat. No. 10,219,852, which is a divisional of U.S. application Ser. No. 14/362,417 filed Jun. 3, 2014, now U.S. Pat. No. 9,636,162, which represents the U.S. National Stage of International Application No. PCT/US2012/067924, filed Dec. 5, 2012, which claims the benefit of U.S. Provisional Patent Application Ser. No. 61/566,891, filed on Dec. 5, 2011, the disclosures of which are incorporated herein by reference in their entirety for all purposes.

STATEMENT REGARDING FEDERALLY SPONSORED RESEARCH

N/A.

BACKGROUND OF THE INVENTION

The present application is directed to systems and methods for surgical rod bending.

Surgical rods are used with bone screws in spine surgery to add stability to and/or correct curvatures of the spine. Surgical rods often have to be contoured to fit a desired curve of the spine and to intersect with sometimes irregular locations of bone screw heads.

Currently, the most common method for imparting complex bends to surgical rods is entirely manual. A surgeon must first determine the desired curvature of the rod by temporarily positioning a flexible surrogate rod in the bone screw heads and bending the surrogate rod by hand until it fits properly in each bone screw head. The surgeon must then remove the surrogate from the surgical table and take the surrogate to a side table where it is used as a visual guide to bend an actual surgical rod with a manual rod-bending tool. This procedure is subjective and can lead to metal fatigue if the surgical rod is accidentally over-bent and then re-bent in the opposite direction. In addition, this method can often subject the surgical rod to an increased risk of surface damage caused by accidental contact with sharp metal tools, resulting in local stress riser points and potential rod breakage after implantation. This method is also time-consuming, especially for inexperienced surgeons.

Attempted solutions to the above manual methods involve automated mapping and bending of surgical rods. For example, some newer systems include an input device that receives or calculates virtual coordinates of a surgical rod with a desired curvature, and a motorized rod-bending device that bends a surgical rod according to the coordinates. More specifically, the coordinates are used to produce bend commands for controlling linear and rotational movement of a straight surgical rod as it is fed through the motorized rod-bending device. The bend commands are also used to control a force-actuating mechanism which bends the surgical rod around a post as it is fed through the motorized rod-bending device.

Common force-actuating mechanisms include bending arms which impose a radial or rotating force on the surgical rod so that the surgical rod bends around the post. These force-actuating mechanisms tend to be bulky and require substantially large systems for applying enough force to bend the surgical rods. In addition, some force-actuating mechanisms fail to provide enough support for the surgical rod to ensure that bending only occurs at the desired points. Other force-actuating mechanisms provide such support but, as a result, impose additional limitations such as restricting the degree of rotation of the surgical rod as it is fed through the rod-bending device. These restrictions limit the range of bending capabilities of the rod-bending device and therefore only permit certain combinations of rotation and bending.

Therefore, it would be desirable to provide a compact system to automatically bend a surgical rod to a desired curvature. Furthermore, it would be desirable to have such system sufficiently support the surgical rod without restricting its range of bending capabilities. Further still, it would be desirable to have methods and apparatuses for detecting a desired curvature of a surgical rod and then outputting dimensional information to such systems for automatic rod bending.

SUMMARY OF THE INVENTION

The present invention overcomes the aforementioned drawbacks by providing an automated surgical rod bending system that permits full rotation of a surgical rod as it passes through the system, independent of previous bends performed along the length of the surgical rod. The present invention additionally incorporates methods for detecting a desired curvature of a surgical rod and outputting such detection information to the automated surgical rod bending system.

It is an aspect of the invention to provide an automated rod bending system to bend a rod. The automated rod bending system comprises a base including a base passage extending therethrough, a linear movement device, a rotational movement device, and a bending device. The linear movement device is configured to axially feed the rod in a first direction through the base passage. The rotational movement device is coupled to one of the base and the linear movement device and is configured to rotate the rod as it is fed through the base passage. The bending device is coupled to the base and includes a roller moveable in a second direction perpendicular to the first direction to impose bending forces against the rod. The automated rod bending system is configured so that the rod is free from contact with the bending device after it is axially fed past the roller.

In another aspect of the invention, an automated rod bending system comprises a plurality of guide rollers, a linear movement device, a rotational movement device, and a bending roller. The linear movement device is configured to axially feed the rod in a first direction between the plurality of guide rollers. The rotational movement device is configured to rotate the rod as it is axially fed between the plurality of guide rollers. The bending roller is configured to impose bending forces against the rod in a second direction perpendicular to the first direction after it is fed between the plurality of guide rollers. The bending roller is positioned adjacent to the plurality of guide rollers so that the imposed bending forces against the rod causes the rod to bend along a curve of one of the plurality of guide rollers.

It is a further aspect of the invention to provide a method for bending a surgical rod. The method includes providing an automated bending system with a bending roller and feeding the surgical rod across the bending roller in a first axial direction. The method also includes rotating the surgical rod relative to the bending roller and forcing the bending roller against the surgical rod in a second axial direction perpendicular to the first axial direction.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 9 is a schematic view of a surrogate rod for use with the present invention.

FIGS. 10A and 10B are schematic side and top views, respectively, of a surrogate rod and an optical scanner for use with the present invention.

FIG. 11 is a schematic view of a digitizing probe for use with the present invention.

DETAILED DESCRIPTION OF THE INVENTION

Figure 1:
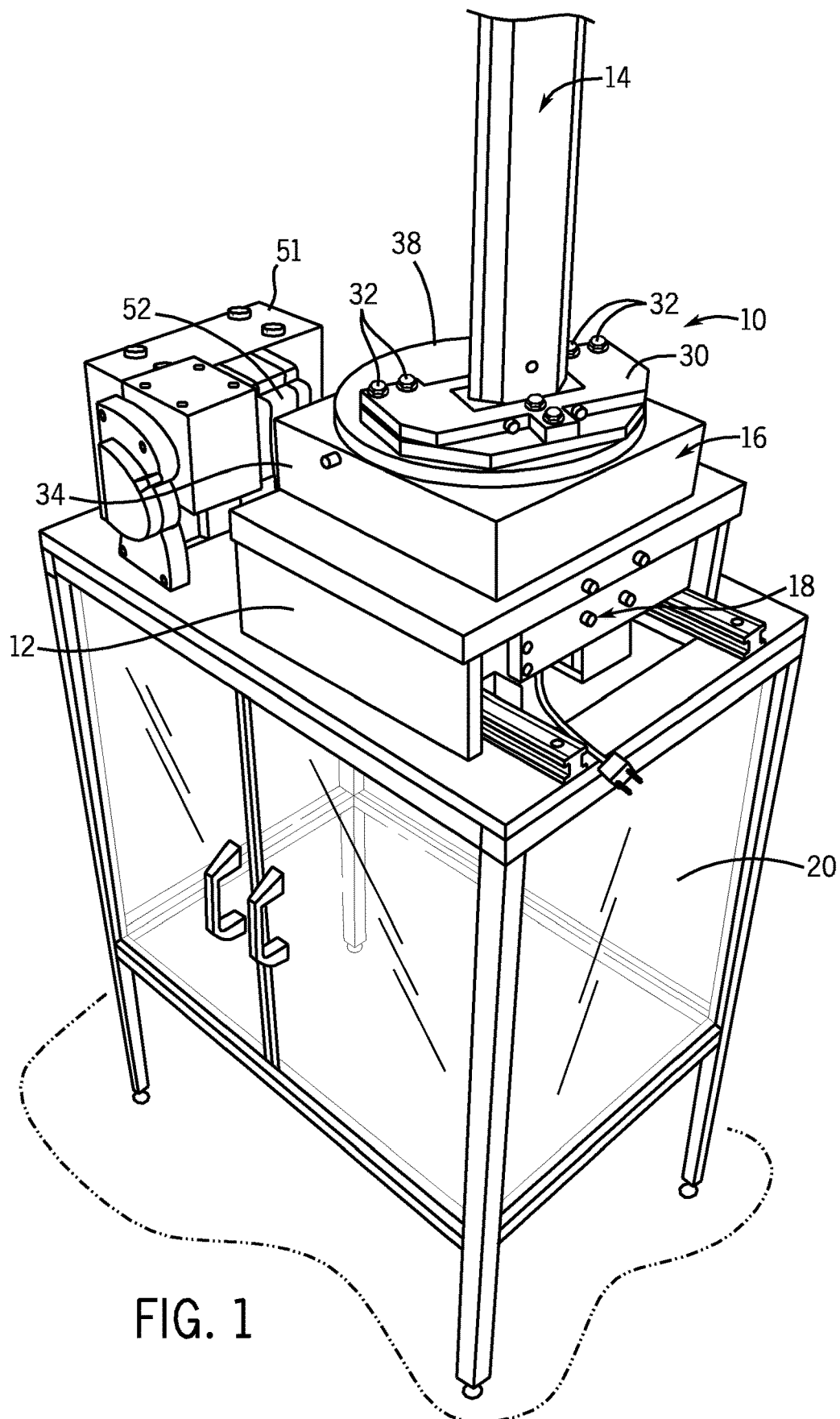
FIG. 1 is a perspective view of an automated surgical rod bending system in accordance with and/or for use with the present invention.

FIG. 1 illustrates an automated surgical rod bending system 10 according to the invention. The system 10 can be used to automatically bend a substantially straight rod to a desired curvature. For example, the system 10 can be used in an operating room to automatically bend an implantable surgical rod for pedicle screw surgery.

Figure 2:
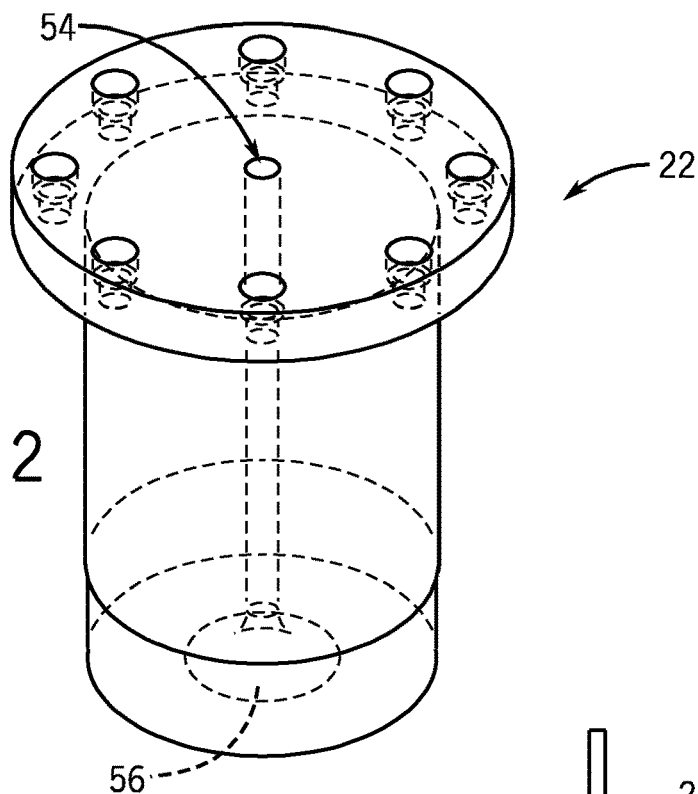
FIGS. 2 and 3 are perspective and cross-sectional schematic views, respectively, of a rod guide for use with the system of FIG. 1.
Figure 3:
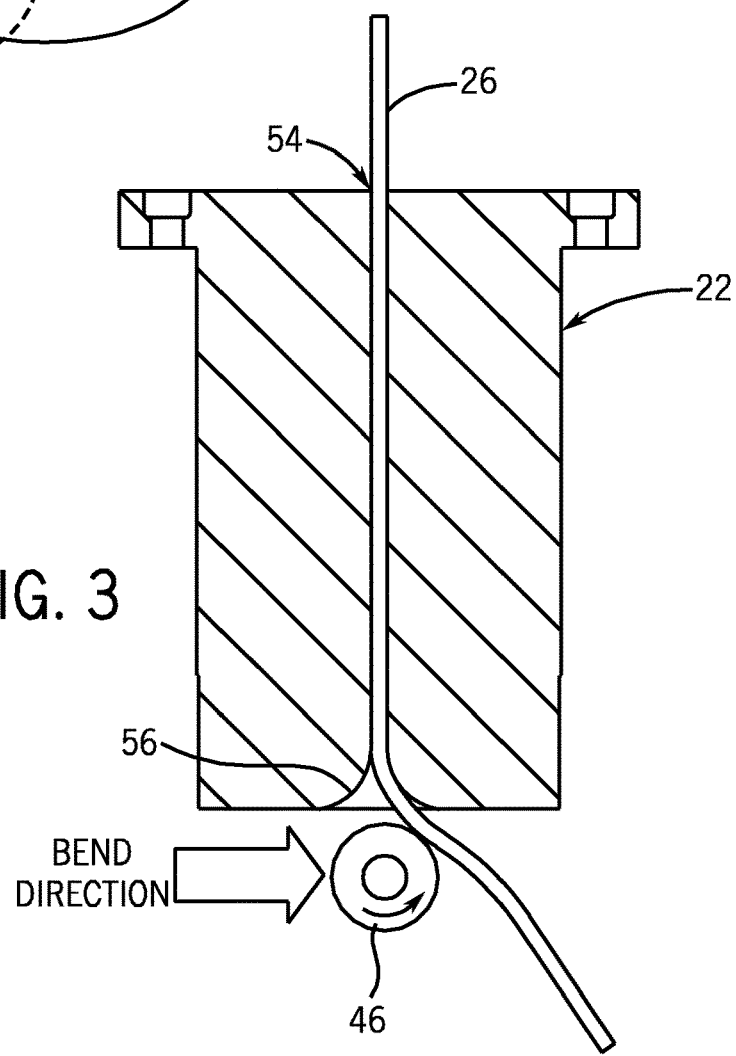

In some embodiments, as shown in FIG. 1, the system 10 can include a base 12, a linear movement device 14, a rotational movement device 16, a bending device 18, a receiving container 20, a rod guide 22 (as shown in FIGS. 2 and 3), and a controller (not shown). The controller can be in communication with and can operate the linear movement device 14, the rotational movement device 16, and/or the bending device 18 (for example, by controlling motors for each device 14, 16, 18, as described below). Also, as shown in FIGS. 4A-5C, the system 10 can include a rod holder 24 coupled to the linear movement device 14 for holding a surgical rod 26. As will be described, the bending device 18 may be designed to also achieve cutting of the surgical rod 26 in addition to bending.

Figure 6:
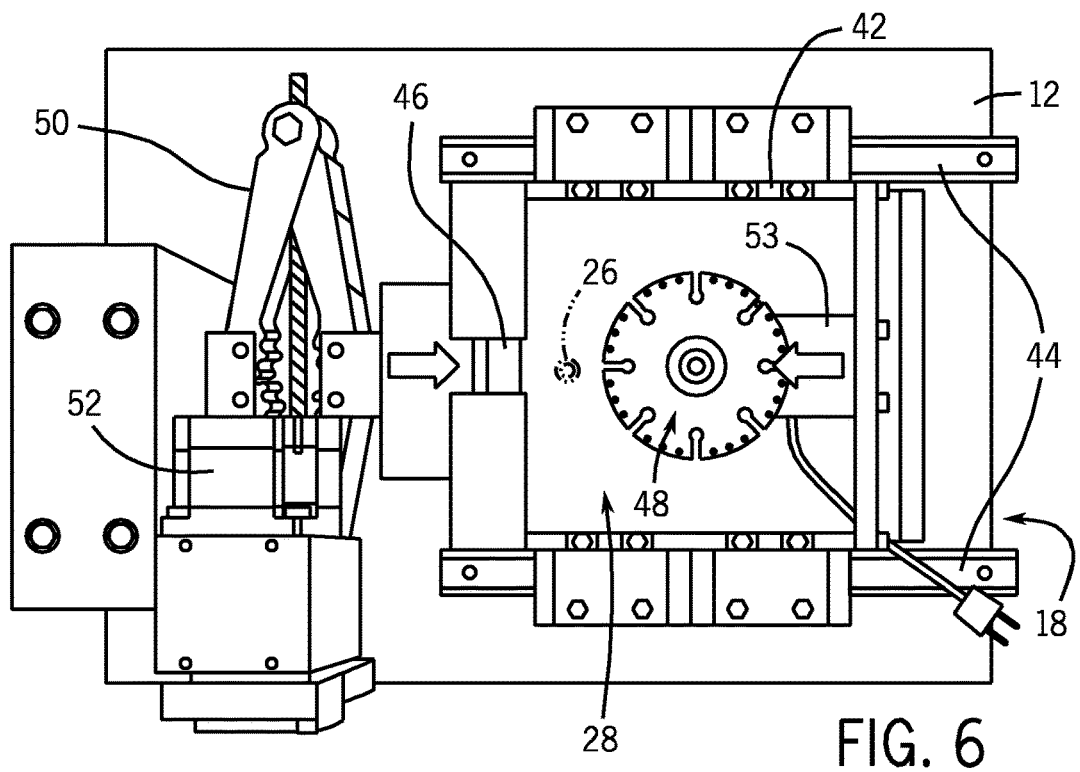
FIG. 6 is a partial top view of the system of FIG. 1.
Figure 7:
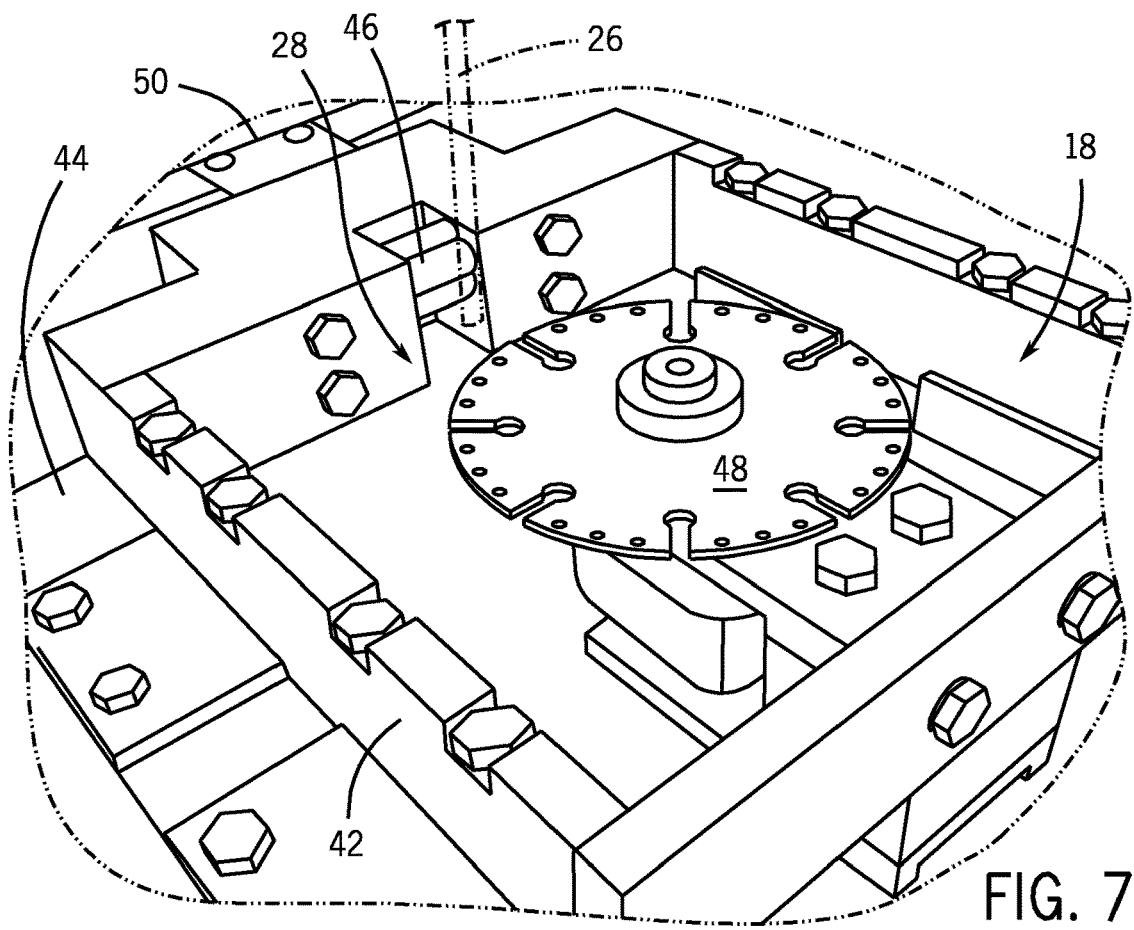
FIG. 7 is a partial perspective view of the system of FIG. 1.

In operation, the system 10 can rigidly hold the trailing end of the surgical rod 26, feed the surgical rod 26 axially through a passage 28 of the base 12 (as best shown in FIGS. 6 and 7), and rotate the surgical rod 26 so that bending can be imposed in a desired direction. More specifically, the surgical rod 26 can be coupled to or secured by the rod holder 24. The controller can operate the linear movement device 14 to vertically feed the surgical rod 26 through the base passage 28 into the receiving container 20. As the surgical rod 26 is fed through the base 12, the bending device 18 can impose bends at different points along the length of the surgical rod 26 and, in some configurations, can cut the surgical rod 26 at a desired length. Further, the rotational movement device 16 can control the rotational orientation of the surgical rod 26 with respect to the bending device 18 as the surgical rod 26 is fed through the base 12.

Figure 4A:
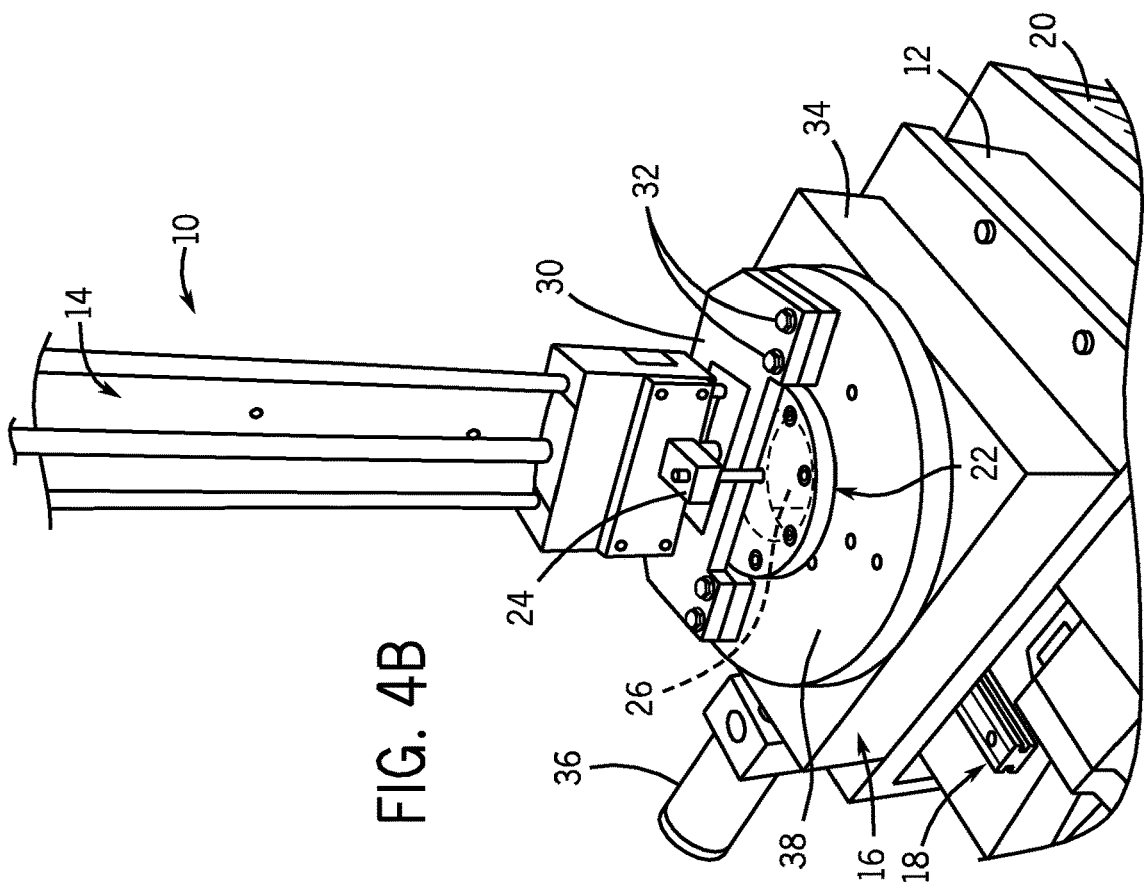
FIGS. 4A and 4B are a series of perspective views of the system of FIG. 1 in different linear positions.
Figure 4B:
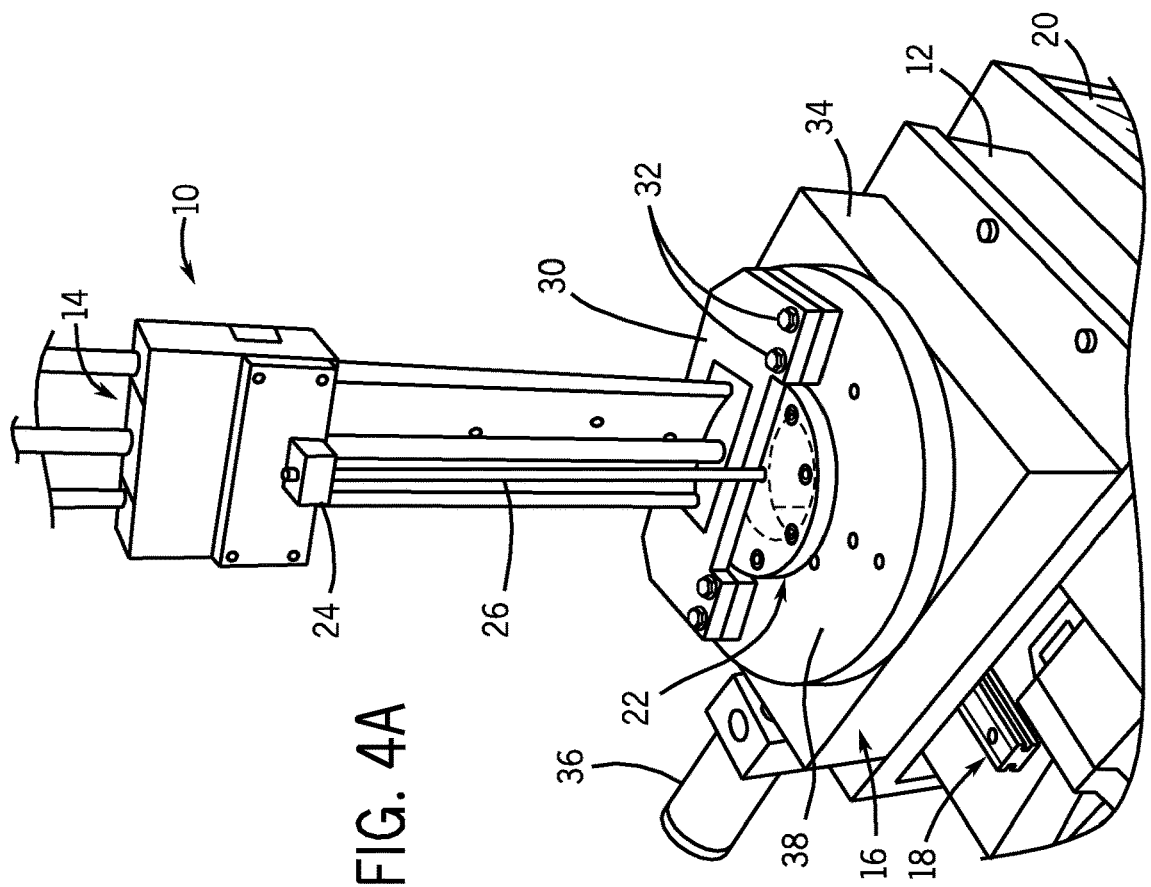
Figure 5B:
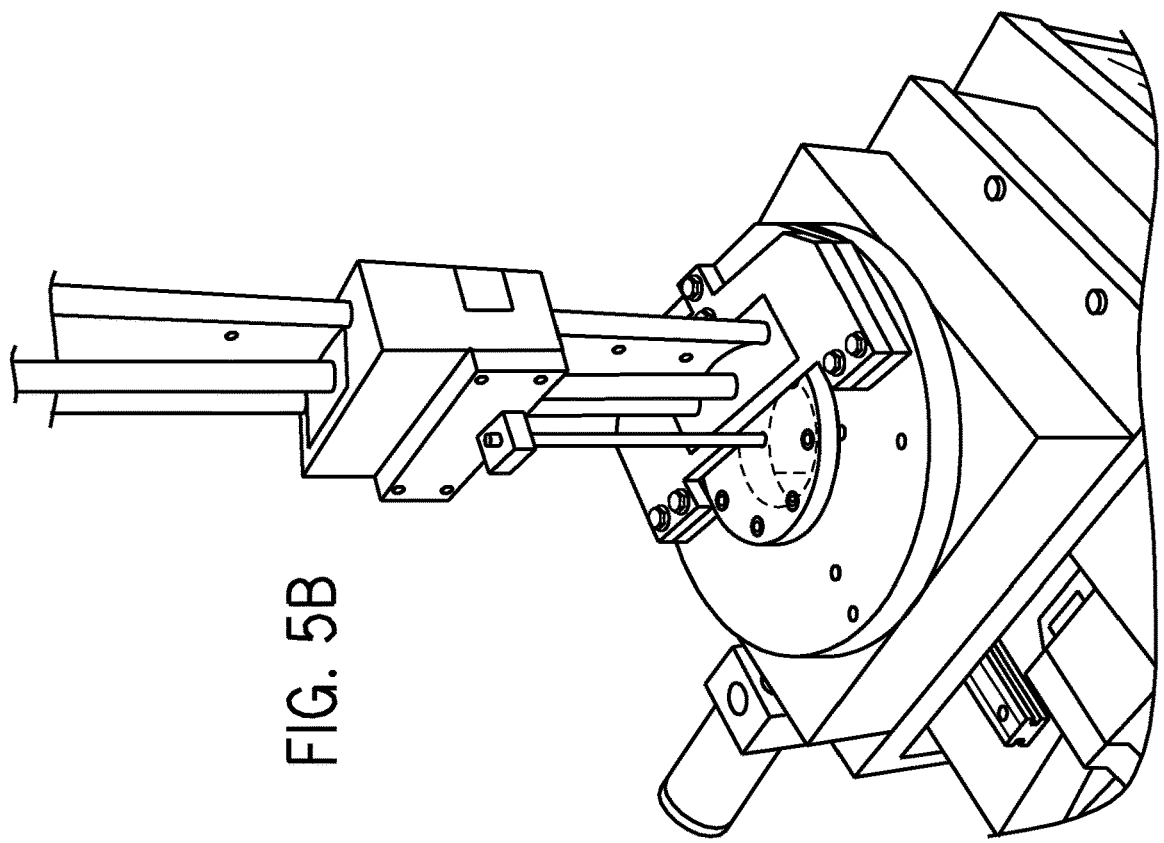
FIGS. 5A-5C are a series of perspective views of the system of FIG. 1 in different rotational positions.
Figure 5A:
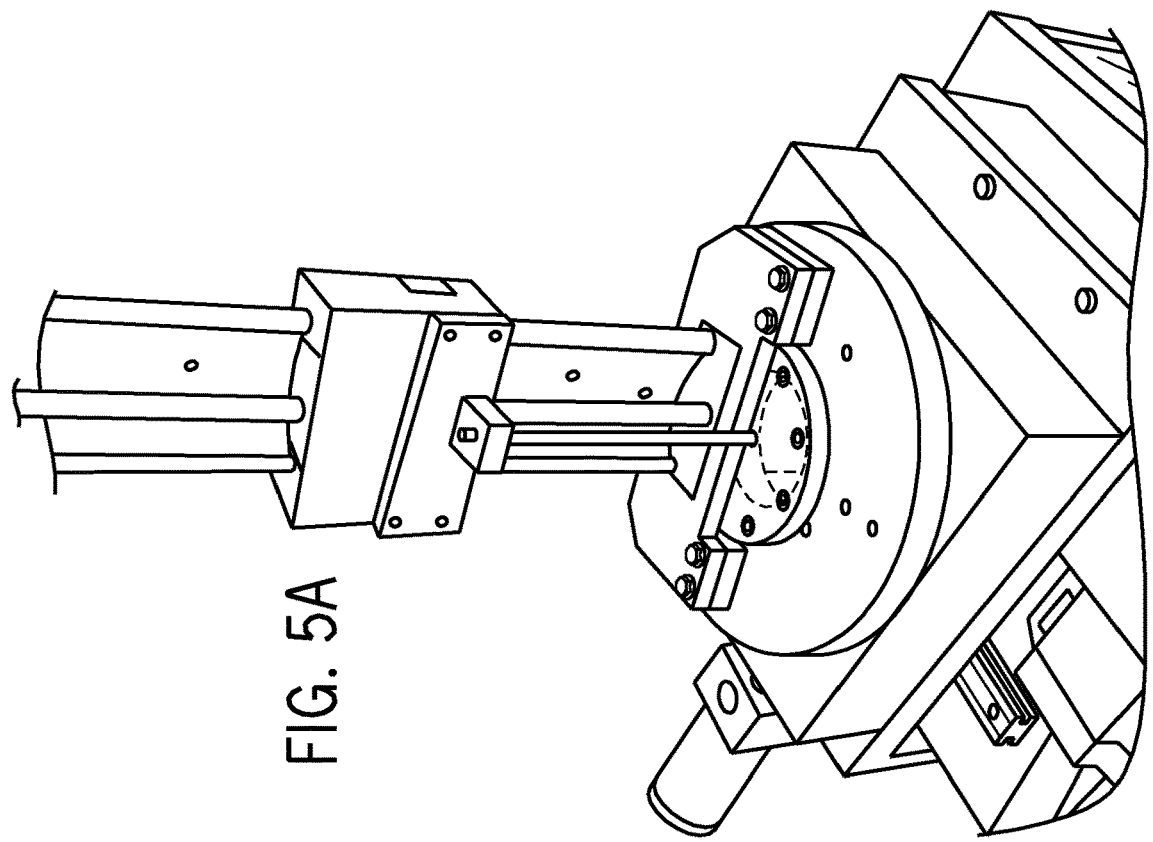
Figure 5C:
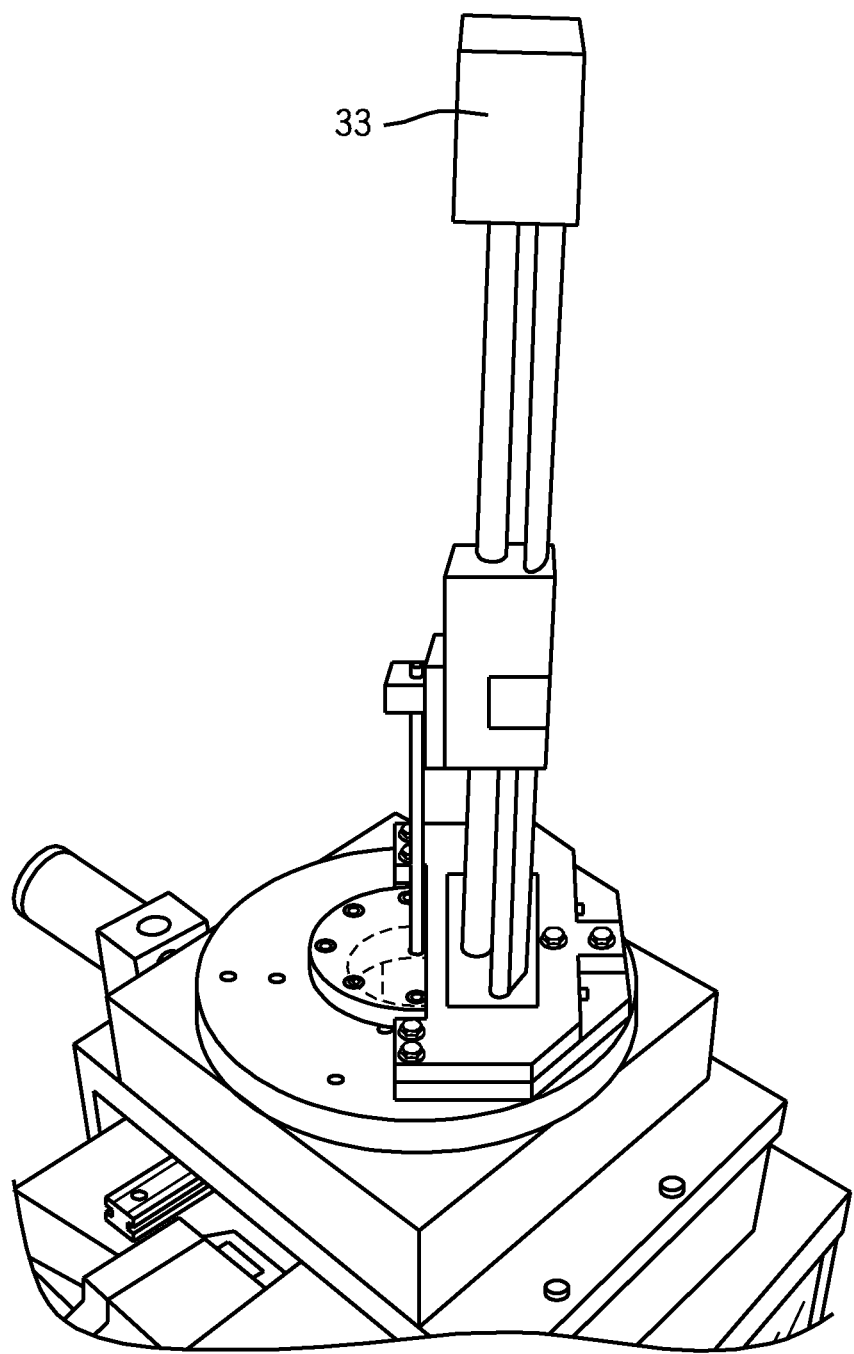

In some embodiments, the linear movement device 14 can be a linear actuator mounted substantially perpendicular to the base 12 and controlled by a first stepper motor 33, as shown in FIG. 5C. The linear movement device 14 can be positioned so that its movement axis is substantially vertical. For example, FIGS. 4A and 4B show the linear movement device 14 in a first position and a second, vertically lower position, respectively. The first stepper motor 33 can control the linear movement device 14 to feed the surgical rod 26 vertically down through the base passage 28 at programmed length increments. In one embodiment, as shown in FIG. 1, the linear movement device 14 can be coupled to the rotational movement device 16 by a coupling mechanism 30 and fasteners 32.

In some embodiments, the rotational movement device 16 can include a rotational actuator 34 mounted substantially parallel to the base 12 and controlled by a second stepper motor 36, as shown in FIGS. 4A-4B. The rotational movement device 16 can also include a rotatable platform 38 coupled to the rotational actuator 34, for example via a rotational bearing (not shown) embedded in the platform 38. The platform 38 can also include a platform passage (not shown) aligned with the base passage 28. The linear movement device 14 can be coupled to the platform 38, as described above, allowing the rotational movement device 16 to control the radial orientation of the linear movement device 14, and thus, the surgical rod 26 with respect to the bending device 18. The second stepper motor 36 can operate the rotational movement device 16 to rotate in one or both directions (that is, positive or negative rotation) between zero degrees and about 360 degrees in programmed increments. For example, FIG. 5A shows the rotational movement device 16 in a first position, FIG. 5B shows the rotational movement device 16 in a second position rotated from the first position by a first degree amount, and FIG. 5C shows the rotational movement device 16 in a third position further rotated from the first position by a second, larger degree amount. In one embodiment, the rotational movement device 16 can be controlled to rotate in increments of about 0.005 degrees.

In some embodiments, the rod guide 22 can be coupled to the platform 38 so that it extends through the platform passage and terminates adjacent to the bending device 18 and/or the base passage 28. As shown in FIGS. 2 and 3, the rod guide 22 can be substantially cylindrical and can include a rod passage 54 for receiving and guiding the surgical rod 26 as it is fed vertically through the platform passage. Bending can be imposed on the surgical rod 26 by the bending device 18 as it exits the rod guide 22.

In some embodiments, the rod passage 54 can terminate with a flared base 56. More specifically, one end of the rod passage 54 (that is, the end adjacent to the base passage 28) can extend radially outward so as to form a outwardly tapering surface that forms a substantial flare outward, as shown in FIGS. 2 and 3. As illustrated, this flared base 56 may advantageously be formed to present a convex surface against which the surgical rod 26 can bend or curve as bending forces are applied by a bending roller 46, as further described below. Other geometries are may be used; however, the flared or convex surface provides an advantageous geometry against which to bend the surgical rod 26 without incurring sharp bends that, for example, may present an unfavorable discontinuous bend (such as those created if the rod is bent too sharply) and/or structural weakness. The cylindrical portion of the rod passage 54 can provide substantial support for the surgical rod 26 to prevent bending or increased stress at other points along the length of the surgical rod 26 as it is bent by the roller 46 and the flared base 56. In one embodiment, the rod guide 22 can rotate with the platform 38 and with the surgical rod 26, allowing bending of the surgical rod 26 to occur against any surface segment of the flared base 56. In another embodiment, the rod guide 22 can remain stationary, allowing the surgical rod 26 to rotate within the rod passage 54 so that bending can occur against the same surface segment of the base 56. In this case, the geometry of the base 56 can be made such that it is only convex on the side against which bending force from the bending device is applied. In addition, in some embodiments, the rod guide 22 can be manufactured from stainless steel or a similar material.

In some embodiments, as shown in FIGS. 6 and 7, the bending device 18 can be coupled to the base 12 and can include a trolley 42 moveable along linear slides 44, a roller 46 coupled to the trolley 42, a cutting wheel 48 coupled to the trolley 42, a scissors jack 50 coupled to the trolley 42, and a third stepper motor 52. The scissors jack 50 allows the bending device 18 to exert large linear forces with a low torque requirement of a driving motor. Other mechanisms for creating linear forces can be used, such as screw drive mechanisms or electromagnetic, hydraulic, or pneumatic piston actuators. The third stepper motor 52 can be operated in forward and reverse to move the scissors jack 50 between a retracted position (as shown in FIG. 6) and an extended position. Extension and retraction of the scissors jack 50 can cause the trolley 42 to traverse across the base passage 28 in a first horizontal direction (for example, away from the third stepper motor 52) and a second horizontal direction (for example, toward the third stepper motor 52). As the surgical rod 26 is vertically fed through the base passage 28, movement of the trolley 42 in the first horizontal direction can allow the roller 46 (for example, a roller bearing) to contact the surgical rod 26, causing the surgical rod 26 to bend. In addition, movement of the trolley 42 in the second direction can allow the cutting wheel 48 to contact and cut the surgical rod 26. In some embodiments, as shown in FIG. 1, the system 10 can include a block 51 or similar stability component coupled to the base 12 and one side of the scissors jack 50 (i.e., the side opposite the trolley 42) can be coupled to the block 51. The block 51 can provide a non-moving part for the scissors jack 50 to press against so that retraction and extension of the scissors jack 50 causes linear movement of the trolley 42.

The third stepper motor 52 and the scissors jack 50 can provide sufficient force to allow the roller 46 to exert bending forces against the surgical rod 26. The increment of distance of travel of the linear movement device 14 and the distance of travel of the bending device 18 toward the surgical rod 26 can affect the type of bend that results. For example, a gentle bend can be imposed by feeding the surgical rod 26 in small increments by advancing the linear movement device 14 and applying minimal displacement of the bending device 18 at each increment, or a sharper bend can be imposed by applying a large displacement of the bending device 18 without incrementing the linear movement device 14, forcing the surgical rod 26 to conform to the flared base 56. In one embodiment, a minimal possible bend curvature imposed on the surgical rod 26 can be dependent on the curvature of the flared base 56. As the name implies, the roller 46 can roll in order to minimize shear forces against the surgical rod 26 as it is bent against the flared base 56.

In addition, in some embodiments, the cutting wheel 48 can be diamond-tipped and/or can be rotatable (for example, by a motor 53, as shown in FIG. 6, connected to an external power source) to permit a substantially clean cut across the surgical rod 26. In other embodiments, the cutting wheel 48 can be substituted with pliers or other mechanical or electrical cutting devices. In some embodiments, components of the linear movement device 14, the rotational movement device 16, and/or the bending device 18 can be manufactured from aluminum and/or stainless steel.

In other embodiments, the base 12 can comprise a different orientation relative to the linear movement device 14, the rotational movement device 16, and/or the bending device 18. For example, the bending device 18 can have a supporting base mechanism that allows it to be oriented at any angle in the plane of the base 12 relative to the platform passage of the bending device 18, thereby allowing bending to occur in more than one direction. In addition, in some embodiments, the bending device 18 may only include components for bending the surgical rod 26, while a separate, independent device includes components for cutting the surgical rod 26, and vice versa.

In conventional rod benders, previous bends may prevent a surgical rod from being rotated in a certain direction to impose subsequent bends. This limitation is often due to such conventional rod benders requiring rod guides that extend past the bending device, or requiring the bend to occur while the rod rests flat against a planar surface. In some embodiments, due to the relative orientation of the linear movement device 14, the rotational movement device 16, the rod guide 22, and the bending device 18, the system 10 may be free of barriers or other components contacting the surgical rod 26 after it passes across the bending device 18 (that is, after it is fed past the roller 46). In addition, the receiving container 20 can be substantially large enough to allow free movement of the surgical rod 26 as it is fed through the base 12 until it is cut by the bending device 18. As a result, the system 10 can allow unlimited rotation of the surgical rod 26 in either direction for subsequent bending, independent of the previous bends made. In addition, in comparison to manual rod bending, the system 10 can produce an accurately bent surgical rod 26 in minimal time.

In some embodiments, the controller can control each of the stepper motors 33 (causing linear actuation), 36 (causing rotation actuation), 52 (causing bending device actuation). In other embodiments, each of the stepper motors 33, 36, 52 can be controlled by individual controllers. Each stepper motor 33, 36, 52 can be pre-programmed to perform its respective movement operations in predetermined increments. For example, the third stepper motor 52 can control movement of the scissors jack 50 in predetermined increments in order to achieve a desired bend. Also, one or more of the stepper motors 33, 36, 52 can be programmed to operate additional components of the system 10. In one embodiment, the controller can control a relay that powers the motor 53 for rotation of the cutting wheel 48. In another embodiment, a switch can be activated to power the cutting wheel motor 53 when the trolley 48 of the bending device 18 crosses an optical sensor or touch sensor (for example, as it moves the cutting wheel 48 in proximity to the surgical rod 26).

In some embodiments, a shield or housing (not shown) can enclose some or all of the components of the system 10. For example, in one embodiment, a protective shield can substantially block access to the bending device 18 during operation of the system 10. In addition, in some embodiments, the system 10 can include a sterilization mechanism (e.g., an autoclave or another suitable sterilization mechanism) to sterilize the surgical rod 26 and/or remove metal debris at the cut locations of the surgical rod 26 after it has passed across the bending device 18.

Figure 8:
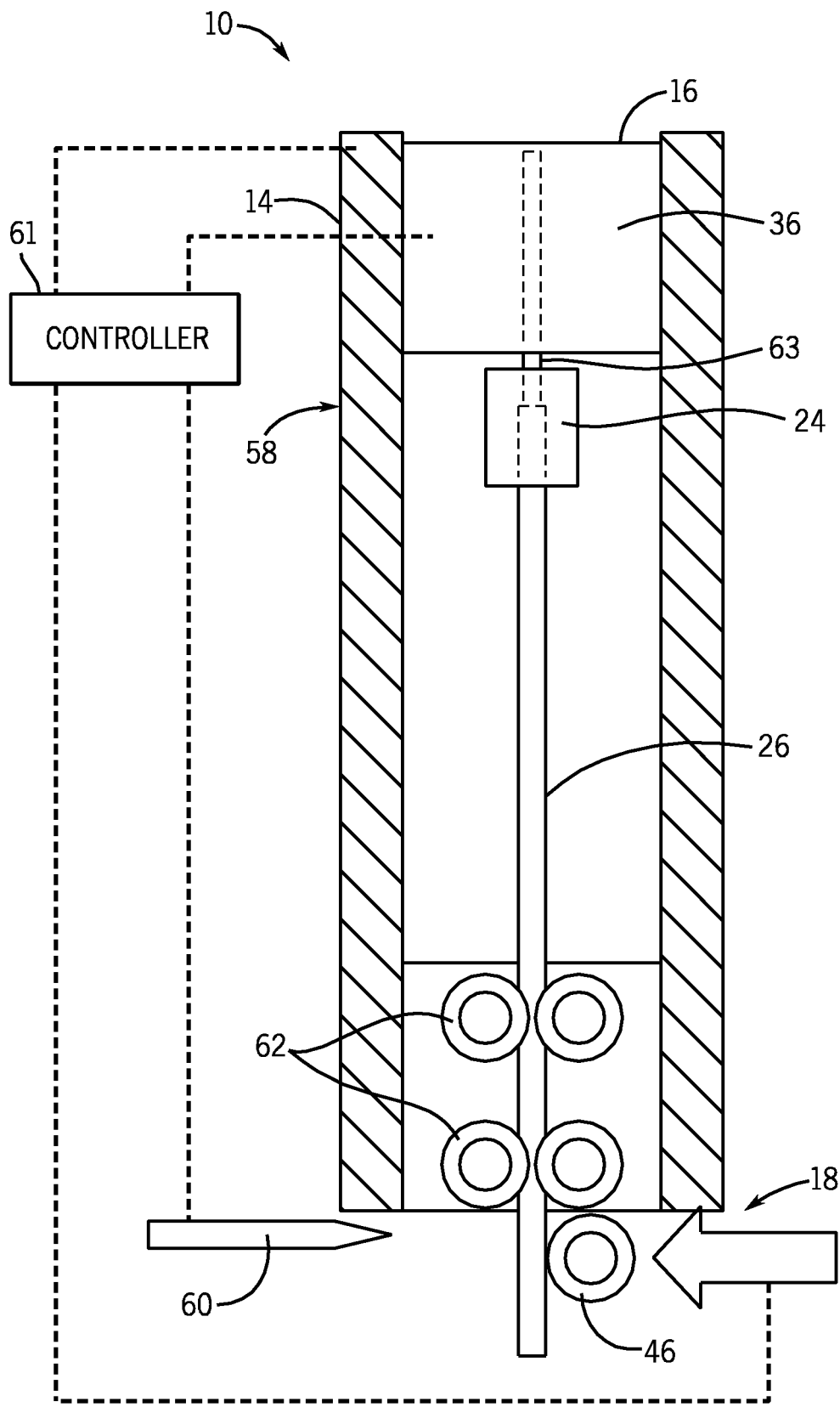
FIG. 8 is a schematic view of an automated surgical rod bending system in accordance with and/or for use with the present invention.

FIG. 8 illustrates the system 10 according to another embodiment of the invention. As shown in FIG. 8, the system 10 can include the linear movement device 14 with linear bearings 58, the rotational movement device 16 including the second stepper motor 36, the rod holder 24, and the bending device or actuator 18 including the bending roller 46 and a cutting blade 60, and a controller 61 (for example, similar to the controller described above with respect to FIGS. 1-7). The system 10 can also include guide rollers 62 that help guide the surgical rod 26 as well as provide a convex surface against which the rod 26 can bend when horizontal force is applied by the bending roller 46.

In the embodiment shown in FIG. 8, the linear movement device 14 can remain stationary, but move the rotational movement device 16 in a linear manner for vertically feed the surgical rod 26 past the bending roller 46. The rotational movement device 16 can cause rotation of the rod holder 24 (for example, via a rotating shaft 63 coupled to the rod holder 24) in order to rotate the surgical rod 26 as it is vertically fed past the bending roller 46. In addition, the horizontal bending forces imposed by the roller 46 against the surgical rod 26 can cause the surgical rod 26 to bend along a curve of one of the guide rollers 62. Once a desired length of the surgical rod 26 has been fed past the roller 46, the cutting blade 60 can be triggered to cut the surgical rod 26.

In some embodiments, the system 10 can be interfaced with an apparatus (not shown) that detects or calculates the desired curvature of a surgical rod and outputs bending commands to the controller 61 of the system 10. The controller 61 can manipulate the position and rotation of the straight surgical rod 26 as it is passed through the system 10 and the amount of travel of the bending roller 46 based on the bending commands.

The apparatus can apply one or more methods for determining or detecting a desired surgical rod curvature. For example, a first method can include optical digitization of a surrogate rod 64, as shown in FIGS. 9-10B. The surrogate rod 64 can have mechanical properties similar to a piece of heavy electrical wire and can be bent by a surgeon by hand (that is, without tools) to align with pedicle screws implanted in a patient. Indicators 66, such as clips or markers, can be applied to the surrogate rod 64 to identify desired termini of the rod, screw head locations, possible bone collision points, etc., as shown in FIG. 9. An optical scanner 68 can then be used to scan the surrogate rod 64 and transmit optical scan information to the apparatus. In one embodiment, the surrogate rod 64 can be fed across the optical scanner 68 at a fixed rate, as shown in FIGS. 10A and 10B. The optical scanner 68 can detect rod angles in two planes, or "x" and "y" location coordinates, along an array of linear "z" positions to provide a three-dimensional optical scan.

The apparatus can analyze the scan information, digitally map a three-dimensional model of the surrogate rod 64, and calculate a proposed curvature of the surgical rod 26 (for example, by applying a mathematical spline fit to the three-dimensional model). The apparatus can then transmit bend commands to the system 10 based on the proposed curvature. Other commands can be determined based on the locations of the indicators. For example, the apparatus can output cutting commands where terminus indicators 66 were located on the surrogate rod 64. The apparatus can also minimize bending of the surgical rod 26 where screw head indicators 66 or possible bone collision indicators 66 were located on the surrogate rod 64. Elimination of bends at these points can permit easier insertion of the surgical rod 26 into the slots in the pedicle screw heads after the rod 26 has been bent.

A second method for defining surgical rod curvature can include a digitizing probe 70, as shown in FIG. 11, and an optical system (such as OptoTrak Certus® system or a similar system) to determine key points along a patient's spine during surgery. A surgeon can use the digitizing probe 70 to identify key points, such as screw heads 72, desired termini of the surgical rod, and/or bony structures that might interfere with the surgical rod, as shown in FIG. 11. Markers on the digitizing probe 70 can allow the optical tracking system to accurately track the location of the probe tip as the surgeon identifies the key points. The apparatus can apply a mathematical spline fit (or another suitable curve fit) to define the desired curvature of the surgical rod based on the key points identified and transmit bend commands to the system 10 based on the defined curvature.

As described above, once curvature is defined using the optical scanning method, the digitization method, or another suitable method, the desired rod curvature can be used to create bend commands for the system 10. The apparatus and/or the controller 61 can make adjustments to the desired rod curvature to minimize bone collisions, bending at screw head locations, binding in the guide tube 54 due to bends by the system 10 that are too sharp, and/or other potential issues. These adjustments can minimize the stresses that surgical rods may experience after they are implanted.

The present invention has been described in terms of one or more preferred embodiments, and it should be appreciated that many equivalents, alternatives, variations, and modifications, aside from those expressly stated, are possible and within the scope of the invention.

The invention claimed is:

1. An automated method for bending a surgical rod, the automated method comprising:
receiving the surgical rod into a plurality of guide rollers;
axially moving the surgical rod in a vertical first direction between the plurality of guide rollers;
applying bending forces against the surgical rod adjacent to the plurality of guide rollers and in a bending plane extending in a second direction perpendicular to the vertical first direction as the surgical rod is engaged with the plurality of guide rollers to cause the surgical rod to bend against a curve of one of the plurality of guide rollers, wherein the surgical rod is unsupported along the bending plane as the rod crosses the bending plane; and
rotating the surgical rod as it is axially moved between the plurality of guide rollers and within a contact-free space adjacent the bending plane that allows rotation of the surgical rod independent of any bends made in the surgical rod.

2. The method of claim 1 further comprising cutting the surgical rod after it is fed between the plurality of guide rollers.

3. The method of claim 1 wherein the bending forces are delivered by a bending roller or bending device and the method further comprises disengaging from contact with the surgical rod after the surgical rod is axially moved past the bending roller.

4. The method of claim 3 further comprising moving a cutting device located adjacent to the bending device in a third direction perpendicular to the first direction and opposite the second direction to cut the surgical rod.

5. The method of claim 1 further comprising controlling the method using a controller and at least one motor programmed based on user input.

6. The method of claim 1 wherein applying the bending forces includes controlling a scissors jack operated by a motor to provide the bending forces.

7. The method of claim 1 wherein applying the bending forces includes controlling a bending roller that is pushed by a motor to provide the bending forces.

8. The method of claim 1 further comprising determining a desired curvature of the surgical rod and determining bend commands based on the desired curvature.

9. The method of claim 8 wherein determining the desired curvature of the surgical rod includes optically scanning a surrogate rod.

10. The method of claim 9 further comprising physically manipulating the surrogate rod to the desired curvature and applying identifiers to the surrogate rod prior to optically scanning the surrogate rod.

11. The method of claim 8 wherein determining the desired curvature of the surgical rod includes digitally mapping points of the surgical rod using a digitizing probe.

12. The method of claim 8 wherein determining the bend commands based on the desired curvature includes mathematically fitting curves to a digital three-dimensional model of the surgical rod using a spline fit.

13. The method of claim 1 further comprising cutting the surgical rod once a desired length has been moved a predefined distance.

* * * * *